United States Patent [19]

Rosenbaum

[11] Patent Number: 5,071,418
[45] Date of Patent: Dec. 10, 1991

[54] ELECTROCAUTERY SURGICAL SCALPEL

[76] Inventor: Joseph Rosenbaum, 23101 Sherman Pl., Canoga Park, Calif. 91307

[21] Appl. No.: 524,031

[22] Filed: May 16, 1990

[51] Int. Cl.$^5$ .............................................. A61B 17/39
[52] U.S. Cl. ........................................ 606/42; 604/35; 606/45; 606/49
[58] Field of Search ................. 606/41, 42, 45, 49; 604/35

[56] References Cited

U.S. PATENT DOCUMENTS

| | | | |
|---|---|---|---|
| 3,974,833 | 8/1976 | Durden, III | 606/49 |
| 4,307,720 | 12/1981 | Weber, Jr. | 606/49 |
| 4,347,842 | 9/1982 | Beale | 606/45 X |
| 4,562,838 | 1/1986 | Walker | 606/45 X |
| 4,719,914 | 1/1988 | Johnson | 606/45 X |
| 4,919,129 | 4/1990 | Weber, Jr. et al. | 606/45 X |

OTHER PUBLICATIONS

*Electrosurgical Coagulating Forceps*, Weck Electrosurgery.
*Product Manual*, Weck Electrosurgery.
*Bovre Operating Room Electrosurgical Products*.

Primary Examiner—Lee S. Cohen
Attorney, Agent, or Firm—Rockey and Rifkin

[57] ABSTRACT

The invention includes an electrosurgical scalpel and a suction/coagulating tool provided in a single surgical instrument. The scalpel assumes an extended position when the instrument is used in a cutting mode and a retracted position when the tool is used in a coagulating mode. A push button control directs either continuous electrical current to the scalpel or pulsed electrical current to the suction/coagulating tool. Suction can be provided during both the cutting and coagulating procedures to maintain a clear field of vision.

11 Claims, 2 Drawing Sheets

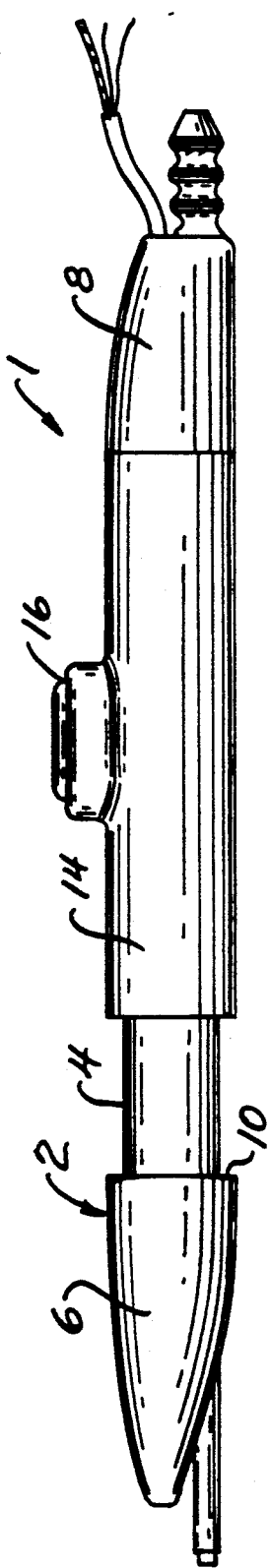
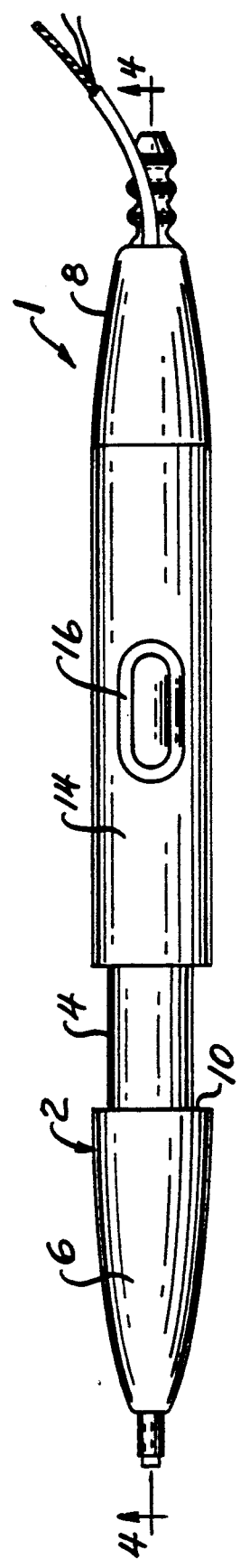
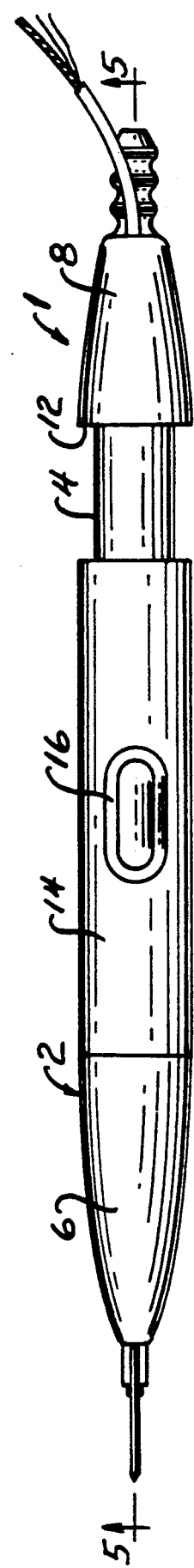

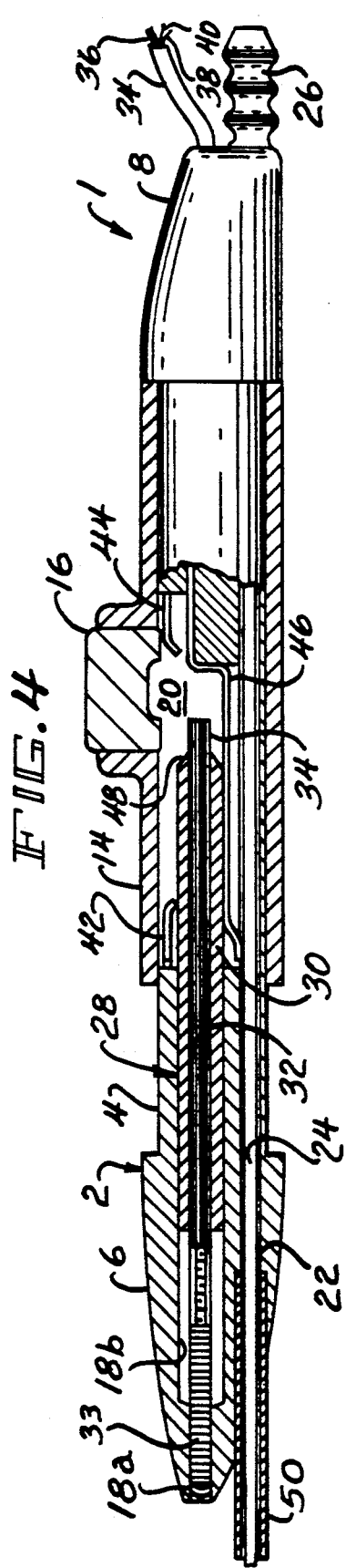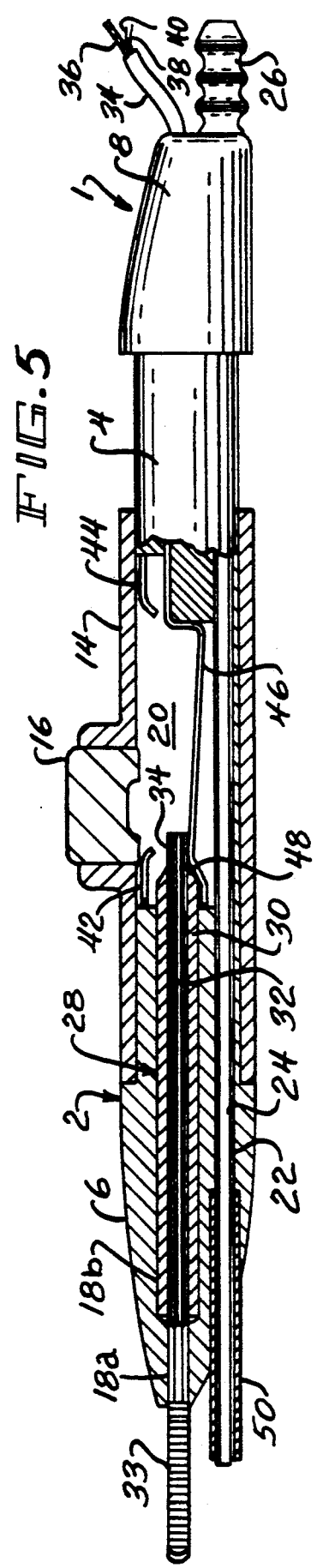

ELECTROCAUTERY SURGICAL SCALPEL

BACKGROUND OF THE INVENTION

The present invention relates, generally, to electrosurgical instruments and, more particularly, to an electrosurgical instrument capable of performing three basic surgical tasks: cutting, suctioning and coagulating.

Electrosurgical instruments such as those sold by Aspen Labs having a scalpel blade capable of operating as both a cutting device and a coagulating device are known in the art. As are electrosurgical coagulation suction tubes such as those sold by Edward Weck and Company, Inc. However, these devices do not include a suction device as an integral part of the instrument such that they are incapable of removing smoke, blood and other debris from the operation situs. As a result, use of the known instruments can impair the surgeon's vision, increasing the difficulty and risk of the surgical procedure.

To alleviate these problems, surgeons must employ a separate suction device while performing the surgical procedures. One shortcoming of using the separate suction device is that both of the surgeon's hands are then occupied, thereby increasing the difficulty of the procedure. Another shortcoming is that the use of a separate suction device makes the precise positioning of the surgical instruments more difficult and cumbersome. Therefore, a single surgical instrument capable of cutting, suctioning and coagulating is desired.

BRIEF DESCRIPTION OF THE INVENTION

The electrosurgical instrument of the invention overcomes the above-noted shortcomings by providing a surgical instrument capable of performing the cutting, coagulating and suctioning tasks. The invention includes an electrosurgical scalpel and a suction/coagulating tool provided in a single surgical instrument. The scalpel assumes an extended position when the instrument is used in a cutting mode and a retracted position when the tool is used in a coagulating mode. A push button control directs either continuous electrical current to the scalpel or pulsed electrical current to the suction/coagulating tool. Suction can be provided during both the cutting and coagulating procedures to maintain a clear field of vision.

OBJECTS OF THE INVENTION

It is a general object of the invention to provide an improved electrosurgical instrument.

It is another object of the invention to provide a surgical instrument capable of performing the three basic surgical tasks: cutting, coagulating and suction.

It is yet another object of the invention to provide an electrosurgical instrument which enhances the surgeon's field of vision.

It is a further object of the invention to provide an electrosurgical instrument in which suction may be continuously applied to the situs of the surgery being either a cutting or coagulating procedure.

It is still a further object of the invention to provide an electrosurgical instrument in which continuous electrical current is supplied to the scalpel and pulsed electrical current is supplied to the suction/coagulating tool.

Other objects of the invention, in addition to those set forth above, will become apparent to one of ordinary skill in the art from the following detailed description of the invention.

BRIEF DESCRIPTION OF THE DRAWINGS

FIG. 1 shows a side view of the invention;

FIG. 2 shows a plan view of the invention with the scalpel in the retracted position;

FIG. 3 shows a plan view of the invention with the scalpel in the extended position;

FIG. 4 shows a section view taken along line 4—4 of FIG. 2; and

FIG. 5 shows a section view taken along line 5—5 of FIG. 3.

DETAILED DESCRIPTION OF THE INVENTION

Referring particularly to FIGS. 1-3, the electrosurgical instrument of the invention is shown generally at 1 consisting of a main body 2 formed of a rigid electrically nonconductive material such as plastic. The main body 2 includes a central portion 4 having a generally cylindrical configuration. The main body 2 also includes a first end portion 6 and a second end portion 8. The end portions 6 and 8 have cross-sectional areas greater than that of central portion 4 such that shoulders 10 and 12 are created at the opposite ends of central portion 4. The end portions 6 and 8 taper as they extend from central portion 4 such that the surgical instrument 1 has a generally ellipsoidal shape.

An annular housing 14 is mounted on central portion 4 and has a length less than that of central portion 4 so as to be freely slidable relative thereto. The movement of housing 14 is limited by shoulders 10 and 12. Rotational movement between the housing 14 and main body 2 is prevented by a key and slot arrangement (not shown) or by any other suitable arrangement that allows the relative reciprocal movement between the housing 14 and main body 2, as will be understood by one of ordinary skill in the art. Reciprocal movement of housing 14 operates to select the desired mode of operation of the instrument as will hereinafter be described.

Housing 14 includes a push button "ON/OFF" control 16 biased to the "OFF" position by a spring (not shown) as will be understood by one of ordinary skill in the art. Push button 16 can be manually depressed to complete the electrical circuit and activate the instrument as will hereinafter be described.

Referring more particularly to FIGS. 4 and 5, main body 2 includes an axially disposed stepped bore having a first section 18a and a second section 18b of greater cross-sectional area. First section 18a communicates with the external environment and second section 18b communicates with a chamber 20 which is centrally located within the main body 2. Chamber 20 is partially bounded by housing 14 such that switch 16 communicates with the interior of chamber 20.

A scalpel plunger 28 is slidably received within bore 18. Scalpel plunger 28 includes a scalpel plunger insulation sleeve 30 dimensioned to be received in bore section 18b. Sleeve 30 is made of electrically non-conductive material such as plastic. Located within sleeve 30 is scalpel plunger 32 made of an electrically conductive material. Scalpel plunger 32 terminates at one end in scalpel blade 33. Scalpel blade 33 is constructed of an electrically conductive material, as is well-known in the art, and is supported in bore section 18a. As shown in FIGS. 4 and 5, the opposite end of scalpel plunger 32 extends beyond the end of sleeve 30 to create a contact surface 34. The function and operation of contact surface 34 will be hereinafter described.

Sleeve 30 is fixedly connected to housing 14 such that reciprocating movement of housing 14 will result in the simultaneous reciprocating movement of sleeve 30. As housing 14 and sleeve 30 are reciprocated between their extreme positions, scalpel blade 33 will be alternatively retracted and extended as shown in FIGS. 4 and 5, respectively.

A second bore 22 is formed in the main body 2 and is located adjacent to bore 18 opposite to switch 16. Bore 22 has a substantially uniform cross-section and extends for the length of the surgical instrument. Bore 22 is positioned such that it intersects chamber 20. A suction tube 24, made of electrically conductive material, is fixed within bore 18. Suction tube 24 is exposed to the interior of chamber 20 where bore 18 intersects chamber 20 and is connected to a vacuum source via conduit 26.

The system for providing electrical power to the scalpel blade 33 and suction tube 24 will be described. Cable 34 provides power from a remote power supply to the surgical instrument 1. Cable 34 includes a heavy gauge braided power lead 36 that carries high frequency current for both the cutting function of scalpel blade 33 and the coagulating function of suction tube 24.

In the cutting mode, the scalpel blade acts as an electrode to heat the fresh tissue such that the cells are dessicated very quickly such that they explode to create an incision. In order to explode the cells, it is necessary to apply the voltage continuously such that the heat delivered per second is high. Thus, the current is delivered as a continuous sinewave as will be understood by one of ordinary skill in the art.

In the coagulating mode, the current is delivered in short pulses with pauses between each pulse as will be understood by one of ordinary skill in the art. In this manner, the voltage used in the coagulating mode and the cutting mode can be the same, yet the average power delivered, i.e., heat per second, is lower in the coagulating mode because of the pauses in the delivery of the current. Thus, the coagulating current can spark the tissue to slowly dehydrate the cells without exploding them as is the result when continuous current is used.

To provide the appropriate current to the instrument 1, signal wires 38 and 40 are provided. When signal wire 38 is connected to power lead 36, continuous or cutting current is delivered. When signal wire 40 is connected to the power lead 30, pulsed or coagulating current is delivered.

To selectively supply the electrical current to either the scalpel blade 33 or the suction tube 24, flexible contacts 42, 44 and 46 are provided. Switch contact 42 is disposed between the push button 16 and the scalpel plunger 28. One end of switch contact 42 is fixed to the wall of the main body 2, the opposite end of flexible switch contact 42 extends into chamber 20. Switch contact 42 is connected to the continuous current signal wire 38 via a conductor (not shown). Power contact 46 has one end supported by the main body 2 such that the other end extends into chamber 20 and is located between the scalpel plunger 28 and the suction tube 24. Power contact 46 is connected to the power lead 36 via a conductor (not shown). Finally, switch contact 44 has one end supported by the main body 2 such that its other end extends into chamber 20 between push button 16 and the power contact 46. Switch contact 44 is connected to the pulsed current signal wire 40 via a conductor (not shown).

In operation, the electrosurgical instrument can operate in either the coagulating mode or the cutting mode. FIGS. 3 and 5 show the instrument in the cutting mode. The housing 14 abuts shoulder 10 such that scalpel blade 33 is in its extended position and push button 16 is located adjacent switch 42.

In this mode, power contact 46 is biased into engagement with contact surface 34 of scalpel plunger 22. When push button 16 is depressed by the surgeon, it will contact switch contact 42 and move it into engagement with contact surface 34. Thus, upon depression of push button 16, the circuit is completed and the power supply will deliver continuous electrical current to scalpel 33 under direction of continuous current signal wire 38. When the push button switch 16 is released, the circuit will be interrupted and current will not flow to scalpel blade 33. It should be noted that in the cutting mode of FIG. 4, suction can be continuously maintained via suction tube 24 such that smoke and debris generated by the cutting procedure will be immediately removed from the cutting situs.

To operate in the coagulating mode, housing 14 is moved to the position shown in FIGS. 2 and 4 such that scalpel blade 33 is retracted and push button 16 is located adjacent flexible switch contact 44. In this mode, switch contact 42 abuts the non-conductive plunger sleeve 30 and is inoperative. Moreover, power contact 46 is moved into engagement with suction tube 24 by plunger sleeve 30. It should be noted that beveled cam surface 48 is provided on plunger sleeve 30 to facilitate the movement of contacts 42 and 46.

When push button 16 is depressed, switch contact 44 will be moved into engagement with power contact 46 such that the circuit is completed and pulsed or coagulating current is provided to suction tube 24 by power contact 46 under signal from pulsed signal wire 40. Because of the application of pulsed current to suction tube 24, the exposed surface 50 of suction tube 24 can perform coagulating procedures. Suction can also be provided simultaneously via suction tube 24 such that smoke and blood generated during the coagulating procedure can be immediately removed from the operation situs. Thus, suction tube 24 and surface 50 operate as a suction/coagulating tool. Because the scalpel blade 33 is retracted during the coagulating procedure, it will not interfere with the coagulating procedure. Release of push button 16 will break the circuit such that current will not flow to the suction tube 24 and the suction operation alone can be performed.

As is evident from the foregoing description, the electrosurgical instrument of the present invention provides a single instrument capable of performing the three basic surgical functions: cutting, coagulating and suctioning. Moreover, the provision for continuous suction and the retractable scalpel blade ensures that the surgeon's field of vision will be unobstructed at all times.

While the embodiments of this invention have been shown and described in some detail, it will be understood that this description and the accompanying drawings are offered merely by way of example, and that the invention is to be limited in scope only by the appended claims.

What is claimed is:
1. An electrosurgical instrument, comprising:

a) first means for performing a coagulating operation;
b) second means for performing a cutting operation;
c) means for moving the second means between an extended position and a retracted position such that when the first means is performing the coagulating operation the second means is in the retracted position and when the second means is performing the cutting operation the second means is in the extended position;
d) means for providing suction during both the coagulating operation and the cutting operation; and
e) means for controlling the operation of the first and second means.

2. The instrument according to claim 1, wherein said means for performing the coagulating operation includes an exposed conductive surface and means for delivering pulsed electrical current to said surface.

3. The instrument according to claim 1, wherein said control means includes a member slidable between a first position in which said coagulating operation can be performed and a second position in which said cutting operation can be performed.

4. The instrument according to claim 3, wherein said member includes a means for selectively delivering either pulsed or continuous current to said first and second means.

5. The instrument according to claim 1, wherein said control means includes a plurality of contacts which can be selectively opened and closed to create a first circuit delivering continuous current to said second means or a second circuit delivering pulsed current to said first means.

6. The instrument according to claim 1, wherein said first means and said means for providing suction are combined in a single tool.

7. An electrosurgical instrument comprising:
(a) a body portion;
(b) a suction tube having a surface of conductive material extending from said body portion;
(c) a scalpel blade supported for reciprocal movement in said body portion;
(d) means for moving said scalpel blade between an extended and retracted position; and
(e) a means for delivering current to said scalpel blade when said scalpel blade is in the extended position and for delivering current to said surface of the suction tube when said scalpel blade is in the retracted position.

8. The instrument according to claim 7, wherein said means for moving said scalpel blade includes a housing slidably supported on said body portion movable between a first position and a second position.

9. The instrument to claim 7, wherein said means for delivering current includes means for delivering continuous current to said scalpel blade and pulsed current to the surface of the suction tube.

10. An electrosurgical instrument, comprising:
a) a body portion;
b) a suction tube having a surface of conductive material extending from said body portion;
c) a scalpel blade supported for reciprocal movement in said body portion;
d) means for moving said scalpel blade between an extended and retracted position; and
e) means for delivering current to said scalpel blade when said scalpel blade is in the extended position and for delivering current to said surface of the suction tube when said scalpel is in the retracted position, wherein the means for delivering current includes a first contact selectively movable into engagement with said scalpel blade, a second contact in continuous engagement with said scalpel blade when said scalpel blade is in the extended position and a third contact selectively movable into engagement with said second contact and said second contact continuously engageable with said surface when said scalpel blade is in said retracted position.

11. The instrument according to claim 10, wherein said means for moving said scalpel blade includes a means for moving said first and third contacts.

* * * * *